United States Patent [19]

Bayer et al.

[11] Patent Number: 4,608,246

[45] Date of Patent: Aug. 26, 1986

[54] TESTING FOR A BLOOD GROUP IMMUNOLOGICAL REACTION

[75] Inventors: William L. Bayer, Jackson County, Mo.; Frederick V. Plapp, Johnson County, Kans.; Malcolm L. Beck, Johnson County, Kans.; Lyle T. Sinor, Johnson County, Kans.; William M. Coenen, Johnson County, Kans.

[73] Assignee: Immucor, Inc., Norcross, Ga.

[21] Appl. No.: 532,464

[22] Filed: Sep. 15, 1983

Related U.S. Application Data

[63] Continuation-in-part of Ser. No. 474,129, Mar. 10, 1983, abandoned.

[51] Int. Cl.$^4$ .......................................... G01N 33/555
[52] U.S. Cl. .......................................... 424/11; 435/7; 435/23; 436/520; 436/521; 436/522; 436/809
[58] Field of Search .................. 424/11; 436/518, 520, 436/521, 522, 809; 435/7, 23

[56] References Cited

U.S. PATENT DOCUMENTS

| | | | |
|---|---|---|---|
| 3,904,367 | 9/1975 | Golibersuch | 436/518 |
| 3,987,159 | 10/1976 | Spona | 424/11 X |
| 4,252,538 | 2/1981 | Barr | 424/11 X |
| 4,275,053 | 6/1981 | Rosenfield | 436/522 |
| 4,328,183 | 5/1982 | Rosenfield | 436/522 X |
| 4,371,515 | 2/1983 | Chu | 436/827 |
| 4,403,037 | 9/1983 | Coates | 424/11 X |

OTHER PUBLICATIONS

"Immunoassays for the 80s", A. Voller et al., eds., Chapter 3 by R. R. A. Coombs, University Park Press, Baltimore, Md., 1981.

*Primary Examiner*—Sidney Marantz
*Attorney, Agent, or Firm*—Kokjer, Kircher, Bradley, Wharton, Bowman & Johnson

[57] ABSTRACT

A method of forward blood grouping is presented wherein known antibodies are attached to a solid surface and the red blood cells presented for immunological reaction are activated with a proteolytic enzyme. A reverse blood grouping procedure utilizes synthetic or purified antigens which are attached directly to a solid surface. The surface is then contacted with an unknown blood component to permit antibodies to undergo immunological reaction with the previously attached antigens. A solution of red blood cells is used as the indicator. A method of performing a major crossmatch utilizes anti-human immunoglobulin that is attached to a solid surface which is then contacted by the two blood components to permit an antigen-antibody interaction of red blood cells and antibodies. The antibody sensitized cells will immunologically adhere to the solid phase. In an alternative major crossmatch procedure, a binder is used to attach red blood cell membranes from a blood donor and the serum from a recipient is allowed to undergo an immune reaction with these membranes on the solid surface. Antibody screening and antibody identification are carried out by attaching known antigen carrying cells to a solid surface. The solid surface is contacted with the unknown solution which will undergo an immune reaction to the extent antibodies specific to the previously adhered antigens are present. Red blood cells or synthetic particles coated with anti-human immunoglobulins are used as the indicator mechanism.

21 Claims, No Drawings

TESTING FOR A BLOOD GROUP IMMUNOLOGICAL REACTION

This is a continuation-in-part of our prior pending application Ser. No. 474,129, filed Mar. 10, 1983, abandoned, and entitled METHOD OF DETECTING AN IMMUNOLOGICAL REACTION.

BACKGROUND OF THE INVENTION

This invention relates generally to immunochemistry and, more particularly, to a method of determining the occurrence or non-occurrence of an immunological reaction between antigens and antibodies.

Blood group serology requires the determination of blood cell compatibility between donor and patient before a transfusion or organ transplant. Blood cell compatibility is determined by the non-occurrence of an immunological reaction between antibodies contained in the blood serum of a patient and antigens present on blood cells from a donor. A patient whose red blood cells are type A (i.e., have "A" antigens on the red cells) will have Anti-B antibodies in his or her serum. Thus, if such a person is given type B blood, an immunological reaction will occur with possible serious clinical consequences.

Blood group serology has most commonly been carried out in liquid phase where the two blood types are interacted and observed for agglutination which indicates that an immunological reaction has occurred. Liquid phase blood group typing is time consuming, somewhat cumbersome, greatly dependent upon the skill of the technician and, to some degree, not sensitive enough to detect all antibodies. A considerable advance in the art of blood group serology is represented by U.S. Pat. No. 4,275,053 to Rosenfield, issued June 23, 1981. This patent is directed to a procedure for conducting blood group serology in solid phase. The disadvantages of liquid phase hemagglutination tests as well as the advantages of working in the solid phase are discussed in detail in the referenced patent, the disclosure of which is specifically incorporated by reference into the subject application. Briefly stated, the Rosenfield patent is directed to a procedure whereby a monolayer of cells of known antigenic composition is irreversibly bound to the walls of a plastic tube. The tube is then contacted with a solution of unknown antibodies which, if they are specific for the antigens of the attached cells, will undergo an immune reaction. The cell layer is lysed and washed to remove hemoglobin. A second solution of known antigen-carrying cells is then applied to the solid matrix in several steps and the extent of the antibody-antigen reaction is measured by the degree to which the second monolayer of cells is immunologically adhered to the antibody layer. The results may be evaluated utilizing densitometric techniques.

It has also been previously demonstrated that viral antibodies can be directly attached to a solid matrix for radio or enzyme linked immunoassays. The technique which has been employed is particularly suitable to non-blood group antibodies and antigens because specific immunoglobulins can be isolated and the investigator is concerned only with a specific reaction. This technology has heretofore not been applied to blood group serology. Furthermore, non-blood group immunological reactions have heretofore relied upon elaborate and time-consuming multiple step processes to attach some type of label, such as radioisotopes, enzymes or fluorophores, to antigens and antibodies in order to measure their participation in an immunological reaction.

SUMMARY OF THE INVENTION

The present invention contemplates a method of testing for ABO forward blood grouping wherein a known antibody is attached directly to a solid surface and an unknown blood sample is activated by treating the sample with an effective quantity of a proteolytic enzyme. The activated sample is then contacted to the solid surface and any antigens specific to the known antibody will undergo immune reaction with the resulting adhered red color on the surface providing an indication of the presence of specific antigens.

The invention also contemplates a method of testing applicable to reverse or serum ABO blood grouping. In this instance, a solid surface capable of supporting an immunological reaction is provided and known antigens are adsorbed onto the surface. The surface is then contacted with an unknown blood component which may contain unknown antibodies specific for the known antigen previously attached, in which case an immune reaction will occur. A solution of red blood cells containing the known antigen first attached to the solid surface is then activated by treating it with an effective quantity of a proteolytic enzyme. This known activated solution is then brought into contact with the solid surface and the known antigens will undergo an immune reaction to the extent antibodies specific thereto were present in the blood component. Any resulting immunologically adhered red color on the surface will indicate the presence of these specific antibodies in the blood component.

Another aspect of the invention is a method of testing applicable to blood group or non-blood group immunological reactions wherein purified natural antigens or antibodies or synthetic antigens or antibodies are attached directly to a solid surface capable of supporting an immunological reaction. The surface is then contacted with a body fluid to permit an immune reaction between any antibody or antigen in the unknown fluid that is specific to an antigen or antibody previously attached to the solid phase. A solution comprising red blood cells and including the known antigen or antibody previously attached is then brought into contact with the surface so that the latter will undergo an immune reaction to the extent antibodies or antigens specific thereto were present in the unknown fluid and have already been immunologically adhered to the solid surface. The resulting red color on the surface will indicate the presence of specific antigens or antibodies in the unknown fluid.

The invention includes a method of testing for a major blood group crossmatch or compatibility test by attaching anti-human immunoglobulin directly to a solid surface. The two blood components to be tested are incubated together and then contacted to the solid phase with the anti-human immunoglobulin attached. Any antibody sensitized red blood cells will adhere to the surface indicating the presence of complementary antibodies and antigens in the two blood components.

A method of antibody screening and antibody identification can also be carried out according to the present invention. A solid surface capable of adsorbing antigens is treated with a binding agent and then contacted with antibody screening cells carrying known antigens. The surface is then contacted with a blood component to allow any antibody in the component to react with any antigens previously attached to the surface. A solution of red blood cells or synthetic particles is coated with anti-human immunoglobulin by a homo- or heterobifunctional chemical binding agent. The solid surface is then contacted with the treated red blood cells or particles which will undergo an immune reaction to the extent antibodies specific thereto have adhered to the solid phase antigens in the previous step. The resulting immunologically adhered red color on the solid phase surface will indicate the presence of antibodies in the unknown samples.

DETAILED DESCRIPTION OF THE INVENTION

Forward ABO Grouping and Rho (D) Typing

The method of the present invention is carried out in solid phase on a solid surface capable of supporting an immunological reaction. Various materials provide adequate solid surfaces acceptable for the present method. Examples of acceptable substrates include beads, test tubes, sheets, strips, and microtiter plates all made of polystyrene or polyvinylchloride. The microtiter plates may have flat bottom, U-shaped or V-shaped wells. It is preferable to use a polystyrene microtiter plate having a U-shaped well. A typical microtiter plate will contain 96 wells allowing multiple testing on a single plate.

Anti-A or B antibody eluates are prepared from red blood cells or known commercial or noncommercial sources of synthetic A or B substances. A titer of at least 1:64 should be achieved for Anti-A and Anti-B eluates. Anti-D eluate is prepared in a similar manner although Anti-D is only attached and eluted from red blood cells. A titer of at least 1:64 should be achieved for Anti-D eluates. The techniques for preparing standardized solutions of Anti-A, Anti-B and Anti-D are well known to those skilled in the art. Alternatively, monoclonal anti-A, B or D antibodies or lectins can be used directly without further processing. It should be noted that the term "solution" as used throughout this specification is intended to encompass whole blood, red blood cell suspensions, serum and other blood components, body fluids and mixtures unless otherwise noted.

The Anti-A and Anti-B solutions are diluted at least 1:20 with 60 millimolar (mM) $Na_2CO_3$, pH 9.6. The diluted solutions are then added to the wells of the microtiter plates, about 100 microliters for a well of 325 microliter capacity. The Anti-A or Anti-B solution is incubated on the solid well surface for up to 18 hours at a temperature of 4° C. or the time may be reduced to one hour if a temperature of about 37° C. is maintained. Intermediate incubation times and temperature ranges are also acceptable. When the preferred microtiter plates having U-wells are employed, care should be taken to assure that the entire concave bottom walls of the wells are adequately coated.

Because Anti-D directly bound to a solid surface does not bind Rh positive red blood cells strongly enough to withstand centrifugal forces, it is desirable to bind Anti-D to anti-human immunoglobulin (IgG) which has first been applied to the surface. Anti-human IgG is available from commercial sources and is incubated on the microtiter plates in a manner well known to those skilled in the art. Anti-D antibody, diluted in saline, is then added as discussed above for Anti-A and Anti-B.

It has been discovered that glutaraldehyde treatment, which has previously been known as a preservative and fixative, will enhance the adherence of the antibody coated plates. Thus, to prolong shelf life of the antibody coated solid surface or enhance the adherence, a dilute glutaraldehyde solution is applied. A 25 weight percent biological grade glutaraldehyde solution is diluted to 2% with 10 mM $NaH_2PO_4$ and 140 mM NaCl; final pH should be about 5. A quantity of about 100 microliters per 325 microliters capacity well is added and incubated for about 2 hours at room temperature. Anti-A, Anti-B or Anti-IgG/Anti-D antibody is then added as discussed above.

In carrying out the method of the present invention, it has been found that considerable advantages result when, in forward blood grouping, the blood being tested is activated with a proteolytic enzyme which is characterized by the ability to modify red blood cells to enhance their serological activity. Examples of suitable proteolytic enzymes for this purpose include Bromelain, Papain, Trypsin Ficin, Proteinase K (protease from *Tritirachium album*), and Pronase (protease from *Streptomyces griseus*). A one-step bromelain method is preferred. A 1% (by weight) stock solution of bromelain in phosphate buffered saline is diluted in additional phosphate buffered saline (pH 7.4) to a final concentration of 0.1%. This has been found to be an effective concentration, though not critical. Some results will be observed at concentrations of 0.05% or less and generally a concentration of greater than 0.5% should be avoided.

Either whole blood or red blood cells at a concentration of 0.5% by volume for red blood cells and 1% by volume for whole blood are then subjected to the bromelain. Again, the concentration levels are not critical and could vary by from one-fifth to five times the amounts stated. Preferably, the whole blood or red blood cells are incubated with the bromelain for 1 to 15 minutes at room temperature.

The bromelain or other enzyme activated blood component (this term encompassing both whole blood and red blood cells) is then added to the individual wells of the previously prepared antibody coated microtiter plates. The blood component can be allowed to settle in the wells unaided although it is preferable to centrifuge for about 30 seconds at 150 times g. Any blood group antigen present in the blood component that is specific for the antibody attached to the well will undergo an immune reaction and adhere to the bottom of the well. A positive reaction is indicated by a uniform effacement of red blood cells over the entire concave bottom surface of the well. A negative reaction will be characterized by all of the red blood cells settling to the bottom of the well into a small "button" in the center. Alternatively, after the red blood cells have been allowed to adhere, the solid surface is washed with 0.85 weight percent NaCl to remove any unreacted and thus unbound red blood cells. Another alternative is to invert the plate and centrifuge for 30 seconds to remove any unbound red blood cells. In these latter two cases, the negative reaction will be indicated by a clear well devoid of red blood cells. The plates may be read visually or mechanically with a densitometer which can be interfaced to a computer for data interpretation and processing.

All of the aforedescribed techniques are applicable to the subsequently described procedures unless noted contra.

Reverse Blood Grouping

The method of the present invention is applicable to reverse ABO blood grouping where known antigens are attached to a solid surface of the type previously specified to determine the presence of specific antibodies. Again, plastic microtiter plates having U-shaped wells are the preferred solid surface. In this application, it has been found particularly advantageous to utilize synthetic A or B substances or purified antigens obtained from either human red blood cell membranes, secretions such as human saliva, or animal tissues such as equine and porcine stomach. These synthetic or purified substances have the advantage that they can be attached directly to the solid surface in the manner previously described for Anti-A and Anti-B antibodies. This results in significant time savings and the synthetic or purified antigens offer greater sensitivity and specificity as well.

In the event that whole blood or a suspension of red blood cells is utilized for the reverse grouping procedure, it is necessary to coat the microtiter plates with a binder such as plant or animal lectins. Suitable substances include *Canavalia ensiformis, Lens culinaris, Pisum sativum, Triticum vulgaris, Glycine max, Limulus polyphemus, Helix pomatia, Helix aspersa,* and *Phaseolus limensis.* The technique for applying the foregoing binders to solid surfaces is well known.

In performing reverse grouping according to the method of the present invention, if whole blood or a suspension of red blood cells are used as the known antigen source, it has been found particularly advantageous to treat the blood component with a proteolytic enzyme as discussed previously in conjunction with forward grouping techniques. Also, when red blood cells or whole blood is used, it is necessary to lyse the cells to remove hemoglobin. This provides a clear background for the detection of positive or negative immune reactions.

The prepared solid surface with antigens attached may be glutaraldehyde fixed in the manner in which the substrates with antibodies attached are glutaraldehyde fixed as discussed above. It is to be noted, however, that with an antigen carrying surface, glutaraldehyde fixation is carried out subsequent to attachment.

Either serum or whole blood may be used for reverse grouping and a sample of the unknown component (this term encompassing both serum and whole blood) is brought into contact with the previously prepared solid surface to allow any antibodies present to bind to the antigens fixed to the solid surface. The unknown blood component is incubated on the solid surface for one to five minutes at room temperature. Next, non-specific antibodies are removed, preferably by washing the surface four times with saline solution. Any blood group antibody specific for the antigen attached to the plate will undergo an immune reaction and adhere to the solid surface. An additional immune reaction is required to indicate the presence of the specific antibodies. For this purpose, a known solution of red blood cells carrying the known blood type antigen is activated with a proteolytic enzyme following the procedure outlined previously in conjunction with the forward blood grouping technique.

The activated solution containing red blood cells carrying the known antigen is then brought into contact with the plate where the unknown component has previously been contacted. A positive reaction indicating the presence of antibodies specific to the known antigen will be indicated by a uniform effacement of red blood cells over the entire concave bottom surface of the well. A negative reaction will be characterized by all of the red blood cells settling to the bottom of the well into a small "button" in the center. Preferably, this final reaction occurs during centrifugation for about one minute at 150 times g. As discussed with the forward grouping procedure, however, the known blood component can be allowed to simply settle in wells unaided for a period of time. Also, as discussed in conjunction with the forward grouping technique, after the known blood component is allowed to adhere, the solid surface may be washed with 0.85 weight percent sodium chloride or centrifuged in an inverted position to remove any unreacted and unbound red blood cells. If this is done, the negative reaction will be indicated by a clear well devoid of red blood cells. The plates may also be read mechanically with a densitometer which can be interfaced to a computer for data interpretation and processing.

Antibody Screening and Antibody Indentification

The method of the present invention can also be utilized for antibody screening utilizing commercially available screening cells carrying 99% or more of the antigens known to exist. The procedure is the same as outlined previously for reverse grouping except that the screening cells are not enzyme activated as this may destroy some antigens. A further departure from the reverse grouping technique is that instead of utilizing indicator red blood cells with the known antigens attached, anti-human immunoglobulin is attached to the indicator red blood cells or synthetic particles in accordance with techniques well known to those skilled in the art. This procedure has been found to offer superior results over a procedure where the known antigens are attached to indicator red blood cells. In carrying out this type of assay, noticeably improved results have been observed when the indicator red blood cells are treated with a hetero or homobifunctional chemical binding agent prior to being brought into contact with the anti-human immunoglobulin. Suitable chemical binding agents include N-succinimidyl (4-azidophenyl)-1,3' dithiopropionate; N-(4-Azidophenylthio) phthalimide; N-Succinimidyl 6-(4'-azido-2'-nitrophenylamino) hexanoate; Glutaraldehyde; Formaldehyde; Dimethyl suberimidate; Dimethyl adipimidate; Dimethyl pimelimidate; Dimethyl-3,3'-dithiobispropionimidate; 2-Iminothiolane; Dithiobis (succinimidylpropionate); Bis [2-(succinimidooxycarbonyloxy)ethyl] sulfone; Disuccinimidyl suberate; Ethylene glycolbis (succinimidyl succinate); Disuccinimidyl tartarate; m-Maleimidobenzoyl N-hydroxysuccinimide ester; Succinimidyl 4-(N-Maleimidomethyl) cyclohexane-1-carboxylate; N-Succinimidyl 3-(2-pyridyldithio) propionate; and Succinimidyl 4-(p-maleimidopyenyl) butyrate. A particularly useful agent is glutaraldehyde. In general, a 1% suspension of saline washed red blood cells should be incubated for thirty minutes in phosphate buffered saline containing 0.01% to 1.0% of the chemical agent. Positive and negative reactions are indicated in the same manner previously discussed in conjunction with reverse grouping. This assay demonstrates the presence (or absence) of antibodies in patient or donor serum which binds to human red blood cells.

The foregoing described technique may also be used for specific antibody identification by attaching known isolated natural or synthetic antigenic determinants to the solid phase matrix.

Direct Antiglobulin Test

The method of the present invention may be adapted for a direct antiglobulin test by coating the U-shaped wells of the microtiter plates with anti-human immunoglobulin according to known techniques. As with the other procedures herein discussed, other solid surfaces can be utilized. Red blood cells which have been coated with human immunoglobulin in vivo will bind specifically to the anti-human immunoglobulin coated solid surface.

This assay will indicate the presence of immunoglobulin on the surface of red blood cells. Positive and negative results are shown in the same manner as discussed under reverse blood grouping. The extent to which sensitized red blood cells are present will be indicated by the immunologically adhered red color over the entire bottom surface of the well. Non-sensitized red blood cells will not bind to the bottom of the well and will settle out as discussed previously.

Major Crossmatch

A major crossmatch may be performed according to the present invention by attaching anti-human immunoglobulin directly to the solid surface. This may be done by means of another antibody, e.g., two animal species may be adhered or one naturally occurring antibody substance may be joined with a monoclonal antibody. The two sources should, of course, be reactive one with the other. The preferred surface is again a microtiter plate with a U-shaped well although other solid surfaces capable of supporting an immunological reaction as previously discussed can be utilized. Preferably, rabbit anti-goat immunoglobulin and goat anti-human immunoglobulin are the two complementary substances utilized. The two blood components to be cross-matched are then incubated for a period of time whereby any antigens and antibodies specific to each other in the two fluids will undergo an immunological reaction. The surface is then contacted with the two blood components whereby any antibody sensitized red blood cells will immunologically adhere to the surface because of the immune reaction with anti-human immunoglobulin. Positive and negative reactions are indicated in the same manner as discussed in conjunction with reverse grouping.

In an alternative procedure, the major crossmatch is carried out by treating the solid surface with a suitable binding agent such as the lectins identified in conjunction with the reverse grouping procedure. The surface is then contacted with the donor's red blood cells (or whole blood) which will adhere to the lectin or other binder. These cells are lysed as discussed in conjunction with reverse grouping. The transfusion recipient's serum is then contacted to the solid surface and any antibodies present in the serum which are specific to antigens in the attached donor's red blood cell membranes will immunologically react and adhere to the solid surface. Indicator red blood cells are coated with anti-human immunoglobulin by using a dilute solution of a chemical binding agent of the type described in conjunction with antibody screening and antibody identification. Alternatively, the anti-human immunoglobulin is attached to some other colored carrier which may be a synthetic substance such as plastic beads. The indicator red blood cells or synthetic particles are allowed to settle or are centrifuged onto the solid surface. If antibody, which was present in the recipient's serum, is bound to the donor's red blood cell membranes on the solid surface, then the indicator red blood cells or beads will immunologically react and adhere to the solid phase. Positive and negative reactions will be indicated in the same manner as discussed in conjunction with antibody screening and antibody identification.

Non-Blood Group Immune Reactions

The method of the present invention is applicable for the detection of non-blood group immune reactions. Any serological test which depends upon an antigen-antibody interaction, utilizing any body fluid, can be carried out according to the present method. Examples of these applications include detection of viral antigens or antibodies in blood or urine (hepatitis, cytomegalovirus, rubella, herpes), bacterial antigens in cerebrospinal fluid (*Hemophilus influenza, Streptococcus pneumoniae, Neisseria menningitidis*), parasites (toxoplasmosis, amebiasis, etc.), human chorionic gonadotopin (pregnancy test), and tumor antigens (e.g., oncofetal proteins).

Immune function testing can also be performed according to the method of the present invention incldu- ing HLA typing, T-helper lymphocyte/T-suppressor lymphocyte ratio, monoclonal antibody screening, and T-cell macrophage interactions.

The basic technique to be followed in testing for a non-blood group immune reaction is that outlined previously for forward blood group testing. That is, a solid surface capable of directly adsorbing antigens or antibodies and supporting an immune reaction is selected. Purified or synthetic substances that will directly attach are utilized. Preferably, a polystyrene microtiter plate having U-shaped wells is utilized. The solid surface is contacted with a known endogenous or exogenous antigen or antibody source to directly attach a layer of the known substance on the surface. Next, the surface is contacted with an unknown body fluid which potentially has either antigens or antibodies present that are specific to the antigens or antibodies previously adhered to the solid surface. Rather than employing a multiple step reaction utilizing some type of indicator mechanism, such as enzymes, fluorophores, or radioisotopes, it has been disovered that red blood cells will perform exceedingly well for this purpose. A solution of indicator red blood cells containing the same known antigen or antibody previously attached to the solid surface is prepared and contacted to the solid surface where the known antigens or antibodies will undergo an immune reaction to the extent antibodies or antigens specific thereto were present in the unknown fluid. The extent of the immune reaction will be indicated by the adhered red color on the solid surface as discussed in conjunction with other test procedures according to the invention. This provides an effective, economical and time efficient indicator which offers considerable advantages over previous indicator mechanisms. As indicated with the forward grouping technique discussed above, the color change on the solid surface can be read mechanically with a densitometer which can be interfaced to a computer for data interpretation and processing.

We claim:

1. A method of testing for a blood group antigen-antibody immunological reaction, said method comprising:
   providing a solid surface capable of adsorbing blood grouping antibodies and supporting an immunological reaction;

contacting said surface with a known blood grouping antibody containing fluid whereby a layer of said antibodies is adsorbed on said surface;

activating an unknown blood sample by treating said sample with an effective quantity of a proteolytic enzyme characterized by the ability to modify red blood cells to enhance their serological activity; and contacting said surface with said activated blood sample whereby any antigen specific to said antibody will undergo an immune reaction with said antibody and the resulting immunologically adhered red color on said surface will indicate the presence of specific antigens in said unknown blood sample.

2. A method as set forth in claim 1, wherein said step of providing a solid surface comprises providing a plate having a well and said contacting steps comprise contacting the bottom wall of said well.

3. A method as set forth in claim 1, wherein said activating step comprises treating said sample with an effective quantity of a proteolytic enzyme selected from the group consisting of Bromelain, Papain, Trypsin, Ficin, Proteinase K, and Pronase.

4. A method as set forth in claim 1, wherein said contacting step comprises incubating said known solution in contact with said surface.

5. A method as set forth in claim 1, wherein said known antibody containing fluid comprises Anti-D and said contacting step comprises first contacting said surface with anti-immunoglobulin substance, incubating said anti-immunoglobulin substance in contact with said surface and then contacting said surface with said Anti-D containing fluid.

6. A method as set forth in claim 1, wherein said method includes, subsequent to said first contacting step, the step of treating said surface with a glutaraldehyde solution.

7. A method of testing for a blood group immunological reaction, said method comprising:
providing a solid surface capable of adsorbing antigens and supporting an immunological reaction;
treating said surface with a binding agent;
providing a quantity of known antigen containing red blood cells for contact with said surface;
activating said known red blood cells with an effective quantity of a proteolytic enzyme characterized by the ability to modify red blood cells to enhance their serological activity;
contacting said surface with said activated known red blood cells;
lysing the surface absorbed known red blood cells to remove hemoglobin;
contacting said surface with an unknown blood component whereby any antibody in said unknown component specific to said antigens in said known red blood cells will undergo an immune reaction with same;
providing a second quantity of said known antigen containing red blood cells; and
contacting said surface with said second quantity of known antigen containing red blood cells whereby said known antigens in said second quantity will undergo an immune reaction to the extent antibodies specific thereto are present in said unknown blood component and any resulting immunologically adhered red color on said surface will indicate the presence of specific antibodies in said unknown blood component.

8. A method as set forth in claim 7, wherein said step of treating said surface with a binding agent comprises treating said surface with a member of the group consisting of plant and animal lectins.

9. A method as set forth in claim 7, wherein said activating step comprises treating said sample with an effective quantity of a proteolytic enzyme selected from the group consisting of Bromelain, Papain, Trypsin, Ficin, Proteinase K, and Pronase.

10. A method of testing for a blood group immunological reaction, said method comprising the steps of:
providing a solid surface capable of direct adsorption of anti-human immunoglobulin substance and supporting an immunolgical reaction;
attaching directly to said surface anti-human immunoglobulin substance;
incubating in direct contact two unknown blood samples whereby any antigens and antibodies specific to each other in said samples will undergo immunological reaction; and
subsequently contacting said surface with said unknown blood samples whereby any antibody sensitized red blood cells will immunologically adhere to said surface indicating the presence of antibodies and antigens specific to each other in said two blood samples.

11. A method as set forth in claim 10, wherein said step of attaching anti-human immunoglobulin comprises attaching same by way of another antibody.

12. A method as set forth in claim 11, whereby said step of providing a solid surface comprises providing a plate having a well and said contacting step comprises contacting the bottom wall of said well.

13. A method of testing for a blood group immunological reaction, said method comprising the steps of:
providing a solid surface capable of adsorbing antigens and supporting an immunological reaction;
treating said surface with a binding agent;
providing a quantity of known antigen containing red blood cells for contact with said surface;
contacting said surface with said known red blood cells whereby a layer of antigens is adsorbed on said surface;
lysing the surface adsorbed red blood cells to remove hemoglobin;
contacting said surface with an unknown blood component whereby any antibody in said unknown blood component specific to said antigens will undergo an immune reaction with same;
providing a second quantity of said known antigen containing red blood cells;
activating said known red blood cells to render same capable of binding anti-human immunoglobulin;
treating said second quantity of red blood cells with anti-human immunoglobulin; and
contacting said surface with said second quantity of known red blood cells whereby said anti-human immunoglobulin in said second quantity will undergo an immune reaction to the extent antibodies specific thereto are present in said unknown blood component and any immunologically adhered red color on said surface will indicate the presence of antibodies in said unknown blood component.

14. A method as set forth in claim 13, wherein said step of providing a solid surface comprises providing a plate having a well and said contacting steps comprise contacting the bottom wall of said well.

15. A method as set forth in claim 13, wherein said activating step comprises subjecting said solution of red blood cells to a solution of a hetero or homo bifunctional chemical binding agent.

16. A method as set forth in claim 15, wherein said step of subjecting said solution of red blood cells to a chemical binding agent comprises subjecting said cells to a member of the group consisting of N-succinimidyl (4-azidophenyl)-1,3' dithiopropionate; N-(4-Azidophenylthio) phthalimide; N-Succinimidyl 6-(4'-azido-2'-nitrophenylamino) hexanoate; Glutaraldehyde; Formaldehyde; Dimethyl suberimidate; Dimethyl adipimidate; Dimethyl pimelimidate; Dimethyl-3,3'-dithiobispropionimidate; 2-Iminothiolane; Dithiobis (succinimidylpropionate); Bis [2-(succinimidooxycarbonyloxy)ethyl] sulfone; Disuccinimidyl suberate; Ethylene glycolbis (succinimidyl succinate); Disuccinimidyl tartarate; m-Maleimidobenzoyl N-hydroxysuccinimide ester; Succinimidyl 4-(N-Maleimidomethyl) cyclohexane-1-carboxylate; N-Succinimidyl 3-(2-pyridyldithio) propionate; and Succinimidyl 4-(p-maleimidophenyl) butyrate.

17. A method as set forth in claim 13, wherein said activating step comprises subjecting said solution of red blood cells to a solution of blood grouping antibodies.

18. A method as set forth in claim 13, wherein said step of subjecting said solution of red blood cells to a chemical binding agent comprising subjecting said cells to a glutaraldehyde solution.

19. A method as set forth in claim 13, wherein said first contacting step comprises contacting said surface with a donor's blood component and said second contacting step comprises contacting said surface with a recipient's blood component.

20. A method of testing for a blood group immunological reaction, said method comprising the steps of:
providing a solid surface capable of adsorption of anti-human immunoglobulin and supporting an immunological reaction;
attaching to said surface a known antibody;
attaching directly to said antibody coated surface anti-human immunoglobulin;
contacting said surface with an unknown blood sample whereby any antibodies present in said unknown blood sample will undergo immunological reaction and adhere to said surface with the resulting adhered red color indicating the presence of said antibodies.

21. A method as set forth in claim 20 whereby said step of providing a solid surface comprises providing a plate having a well and said contacting step comprises contacting the bottom wall of said well.

* * * * *